United States Patent [19]
Chan

[11] 3,960,931
[45] June 1, 1976

[54] 1,2-DIPHENYL-ETHANE DERIVATIVES

[75] Inventor: Rosalind Po-Kuen Chan, Hong Kong, Hong Kong

[73] Assignee: Biorex Laboratories, Limited, England

[22] Filed: Mar. 11, 1974

[21] Appl. No.: 450,242

[30] Foreign Application Priority Data
Mar. 23, 1973 United Kingdom............... 14048/73

[52] U.S. Cl. ..................... 260/479 R; 260/613 R; 260/618 B; 260/619 B; 424/311; 424/341; 424/346; 424/347

[51] Int. Cl.² .................. C07C 39/16; C07C 43/20; C07C 69/14

[58] Field of Search ......... 260/479 R, 619 B, 613 R

[56] References Cited
FOREIGN PATENTS OR APPLICATIONS

| | | | |
|---|---|---|---|
| 37-2617 | 5/1962 | Japan .............................. | 260/619 B |
| 111,456 | 8/1944 | Sweden .......................... | 260/619 B |
| 596,957 | 1/1948 | United Kingdom ............. | 260/619 B |

OTHER PUBLICATIONS
Yale J. Med. Pharm. Chem., vol. No. 2, (1959), pp. 121–133.
Merck Index, 6th Ed., p. 495.
Dodds et al., Proc. Roy. Soc., (London), vol. 127 B, pp. 140–143.

*Primary Examiner*—James A.≅ Patten
*Attorney, Agent, or Firm*—Wenderoth, Lind & Ponack

[57] ABSTRACT

The present invention provides new 1,2-diphenyl-ethane derivatives of the general formula:

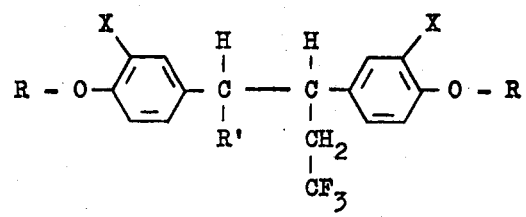

wherein R is a hydrogen atom or an alkyl or acyl radical, X is a hydrogen or halogen atom and R' is an alkyl radical.

16 Claims, No Drawings

1,2-DIPHENYL-ETHANE DERIVATIVES

BACKGROUND OF THE INVENTION.

There is an increasing demand for compounds which can be used for oestrogen replacement therapy in deficiency states and for the control of contraception.

Certain 1,2-diphenyl-ethane derivatives are already known which are of some use for the above-mentioned indications and the present invention provides a new group of 1,2-diphenyl-ethane derivatives which are superior to those already known.

SUMMARY OF THE INVENTION.

The new 1,2-diphenyl-ethane derivatives according to the present invention are threo and erythro compounds of the general formula:

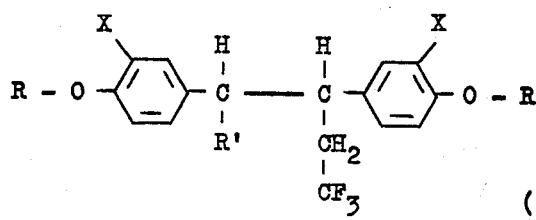

wherein R is a hydrogen atom or an alkyl or acyl radical, X is a hydrogen or halogen atom and R' is an alkyl radical.

DETAILED DESCRIPTION OF THE INVENTION.

The alkyl radicals R and R' in the above general formula preferably contain up to 6 carbon atoms and more preferably up to 3 carbon atoms and can be straight-chained or branched, for example, methyl, ethyl, n-propyl, isopropyl, n-butyl, isobutyl, tert.-butyl and n-hexyl radicals. The acyl radicals R in the above general formula are preferably derived from aliphatic carboxylic acids containing up to 6 carbon atoms and more preferably up to 3 carbon atoms, for example, acetic acid, propionic acid, butyric acid and valeric acid.

The new compounds of general formula (I) can be prepared from a deoxyanisoin compound of the general formula:

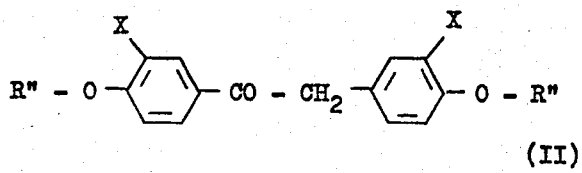

wherein R'' is an alkyl radical and X has the same meaning as above, by reaction with trifluoroethyl iodide to give a compound of the general formula:

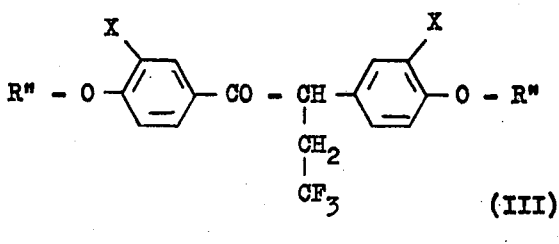

wherein R'' and X have the same meanings as above, which is then reacted with an alkyl magnesium iodide to give a carbinol of the general formula:

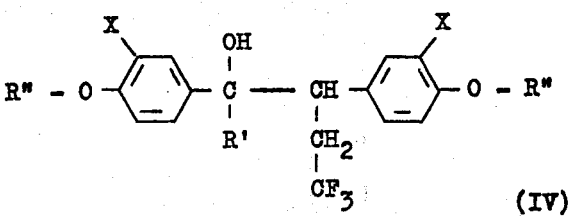

wherein R', R'' and X have the same meanings as above, this carbinol is then hydrogenated and the hydrogenation product crystallised to give a compound of the general formula:

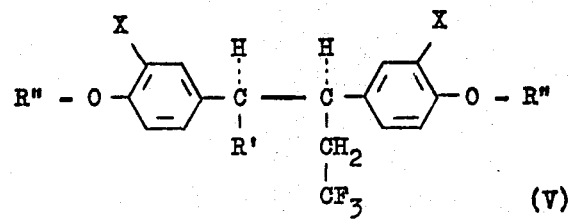

wherein R', R'' and X have the same meanings as above, which, if desired, can then be dealkylated to give the corresponding dihydroxy compound (I, R = H), whereafter, if desired, this dihydroxy compound can then be acylated.

The reaction with trifluoroethyl iodide is preferably carried out in an inert solvent at an elevated temperature in the presence of an alkali metal hydride, for example sodium hydride.

The reaction with the alkyl magnesium iodide is preferably carried out in an inert solvent, such as diethyl ether, under reflux.

The hydrogenation of the carbinol (IV) is preferably carried out with the use of hydrogen in the presence of a catalyst, for example, palladium on charcoal.

The optional dealkylation can be carried out, for example, by the action of hydrobromic acid in acetic acid.

The subsequent optional acylation can be carried out, for example, by reaction with a reactive derivative of an appropriate carboxylic acid, for example, an acid anhydride in the presence of pyridine or an acid halide in the presence of an acid-binding agent to remove the hydrohalide formed as by-product.

When a product is obtained in which X is a hydrogen atom, then, if desired, it can subsequently be halogenated, for example with elemental bromine or with sulphuryl chloride.

The following Examples are given for the purpose of illustrating the present invention:

EXAMPLE 1 a. A solution of 7.68 g. (0.03 mole) dry deoxyanisoin in 200 ml. dry dimethyl formamide was mixed with 1.44 g. sodium hydride (50% dispersion) and the mixture was stirred for 2 hours. 6.5 g. trifluoroethyl iodide were added to the dark green solution obtained and the reaction mixture was heated at 40° – 50°C. for 2 hours. After cooling, the solution was poured into a mixture of ice and dilute hydrochloric acid and extracted with ether. The etheral extract was evaporated to give an oil which was dried by evaporation with benzene and purified by passing a benzene solution of the product through 100 g. alumina. Evaporation of the benzene eluate gave an oil, which was $\alpha$-trifluoroethyl-deoxyanisoin.

b. A solution of methyl magnesium iodide in ether was prepared from 1 g. magnesium and 7 g. methyl iodide. To this was added a solution of the above $\alpha$-trifluoroethyl-deoxyanisoin in 50 ml. anhydrous ether. The reaction mixture was refluxed for 4 – 5 hours, cooled and poured into a mixture of ice and dilute hydrochloric acid. This was extracted with ether and the ethereal extract was evaporated to give an oil, which was dried by benzene evaporation. The product obtained was 4,4'-dimethoxy-$\alpha$-methyl-$\alpha$-hydroxy-$\alpha'$-trifluoroethyl-bibenzyl.

c. This hydroxy compound was then introduced into a mixture of 70 ml. glacial acetic acid and 0.5 ml. perchloric acid and shaken with hydrogen in the presence of 1 g. palladium on charcoal (10%) for 6 hours. The reaction mixture was filtered and the filtrate was diluted with water and extracted with ether. The ethereal extract was washed with water and then with a dilute aqueous solution of sodium hydroxide and thereafter dried and evaporated. The residue was crystallised from methanol to give 3.5 g. of a solid which was recrystallised from methanol to give pure erythro-4,4'-dimethoxy-$\alpha$-methyl-$\alpha'$-trifluoroethyl-bibenzyl, which had a melting point of 81° – 83°C.

d. 3 g. of this dimethoxy compound were then heated under reflux for 4 hours, in an atmosphere of nitrogen, with 70 ml. glacial acetic acid and 40 ml. hydrobromic acid. After cooling, the solution was diluted with water and extracted with ether. The ethereal extract was washed with water and with an aqueous solution of sodium bicarbonate, dried and evaporated to dryness. The residue was recrystallised from benzene to give pure erythro-4,4'-dihydroxy-$\alpha$-methyl-$\alpha'$-trifluoroethyl-bibenzyl, which had a melting point of 156° – 157°C.

EXAMPLE 2.

a. A solution of 6 g. m,m'-difluorodeoxyanisoin (m.p. 140° – 149°C.) in 200 ml. dimethyl formamide was mixed with 1 g. sodium hydride (50% dispersion) and stirred for 2 hours. 6 g. trifluoroethyl iodide in 10 ml. dimethyl formamide were added to the green solution obtained and the reaction mixture was heated to 40° – 50°C. for 3 hours. After cooling, the reaction mixture was poured into a mixture of ice and dilute hydrochloric acid and this then extracted with ether. Evaporation of the ethereal extract gave m,m'-difluoro-$\alpha$-trifluoroethyl-deoxyanisoin in the form of an oil which was purified by dissolving in 100 ml. dry benzene and passing the solution through 100 g. alumina. Thin layer chromatography showed it to be free of starting materials and of other contaminants. The yield was 6.5 g.

b. The above oil was dissolved in 50 ml. ether and mixed at 0° – 5°C. with an ethereal solution of methyl magnesium iodide, prepared from 1 g. magnesium and 14 g. methyl iodide. The reaction mixture was heated under reflux for 4 hours, cooled and then poured on to a mixture of ice and hydrochloric acid. This was then extracted with ether and the ethereal extract was evaporated to give 3,3'-difluoro-4,4'-dimethoxy-$\alpha$-methyl-$\alpha$-hydroxy-$\alpha'$-trifluoroethyl-bibenzyl.

c. This hydroxy compound was introduced into a mixture of 80 ml. glacial acetic acid and 0.5 ml. perchloric acid and shaken with hydrogen in the presence of 1 g. palladium on charcoal (10%) until the take up of hydrogen ceased. The acidic solution was filtered and the filtrate was diluted with water and extracted with ether. The ethereal extract was washed, dried and evaporated and the residue recrystallised from methanol to give 2.5 g. pure erythro-3,3'-difluoro-4,4'-dimethoxy-$\alpha$-methyl-$\alpha'$-trifluoroethyl-bibenzyl, which had a melting point of 103° – 104°C.

d. 2.4 g. of this bibenzyl compound were heated at 140° – 145°C. for 6 hours in a mixture of 60 ml. glacial acetic acid and 30 ml. hydrobromic acid, in an atmosphere of nitrogen. The reaction mixture was then diluted with water and cooled to bring about crystallisation. The product obtained was recrystallised from benzene to give pure erythro-3,3'-difluoro-4,4'-dihydroxy-$\alpha$-methyl-$\alpha'$-trifluoroethyl-bibenzyl, which had a melting point of 152°C.

EXAMPLE 3.

a. A solution of 10 g. m,m'-difluoro-$\alpha$-trifluoroethyl-deoxyanisoin (see Example 2a)) in 100 ml. anhydrous ether was added dropwise, while stirring, to a solution of n-propyl magnesium iodide in ether (prepared from 8.1 g. n-propyl iodide and 1.2 g. magnesium in 100 ml. anhydrous ether). When the addition was complete, the reaction mixture was heated under reflux for 3 hours and then cooled and poured into a mixture of ice and dilute hydrochloric acid, followed by extraction with ether. The ethereal extract was washed with an aqueous solution of sodium bisulphite and then with water, dried over anhydrous sodium sulphate and evaporated to dryness to give 11 g. of oily 3,3′-difluoro-4,4′-dimethoxy-α-(n-propyl)-α-hydroxy-α′-trifluoroethyl-bibenzyl.

b. This hydroxy compound, in 70 ml. glacial acetic acid containing 2 drops of perchloric acid, was hydrogenated over 1.2 g. palladium on charcoal (10%) until the absorption of hydrogen ceased. The catalyst was then filtered off and the filtrate diluted with water, followed by extraction with ether. The ethereal solution was washed with water and with a dilute aqueous solution of sodium hydroxide, dried over anhydrous sodium sulphate and evaporated to dryness. The residue was recrystallised from methanol to give 1 g. erythro-3,3′-difluoro-4,4′-dimethoxy-α-(n-propyl)-α′-trifluoromethyl-bibenzyl, which had a melting point of 188° – 190.5°C. The mother liquor contained 7 g. of material which was shown by gas chromatography to contain over 95% by weight of the oily threo isomer.

c. A mixture of 700 mg. of the above erythro compound, 10 ml. hydrobromic acid and 20 ml. glacial acetic acid was heated in an atmosphere of nitrogen at 145°C. for 5 hours. The reaction mixture was then diluted with water and cooled to 0°C. to bring about crystallisation. 500 mg. of crystals were thus obtained which were recrystallised from ether-petroleum ether (1:2) to give erythro-3,3′-difluoro-4,4′-dihydroxy-α-(n-propyl)-α′-trifluoroethyl-bibenzyl, which had a melting point of 137° – 138°C.

EXAMPLE 4.

a. To an ethereal solution of n-propyl magnesium iodide (prepared from 0.07 molar n-propyl iodide and magnesium in 100 ml. ether) was added, while stirring, a solution of 16.9 g. (0.05 mole) α-trifluoroethyl-deoxyanisoin (see Example 1a)) and the reaction mixture was heated under reflux for 3 hours, whereafter it was poured into ice - dilute hydrochloric acid and extracted with ether. The ethereal extract was washed with water and an aqueous solution of sodium bisulphite, dried and evaporated to dryness. There was obtained an oily residue of 4,4′-dimethoxy-α-(n-propyl)-α-hydroxy-α′-trifluoroethyl-bibenzyl.

b. This oily hydroxy compound, in a mixture of 100 ml. glacial acetic acid and 0.2 ml. perchloric acid, was hydrogenated over 2 g. palladium on charcoal (10%). The catalyst was then removed and the solution diluted with water and extracted with ether. After drying and evaporating the ethereal extract, there were obtained 4 g. of solid which was recrystallised twice from methanol to give erythro-4,4′-dimethoxy-α-(n-propyl)-α′-trifluoroethyl-bibenzyl, which had a melting point of 148° – 150°C. The mother liquor contained 9.2 g. of the threo isomer, which had a melting point of 82° – 84°C.

c. 3 g. of the erythro isomer were demethylated by heating for 5 hours at 150°C. in 30 ml. glacial acetic acid and 15 ml. hydrobromic acid under an atmosphere of nitrogen. After working up the reaction mixture in the usual way, there were obtained 2.5 g. erythro-4,4′-dihydroxy-α-(n-propyl)-α′-trifluoroethyl-bibenzyl which was recrystallised from ether-petroleum ether (1:2), whereafter it had a melting point of 186° – 187°C.

EXAMPLE 5.

a. A solution of 2 g. erythro-4,4′-dihydroxy-α-methyl-α′-trifluoroethyl-bibenzyl (see Example 1) in 50 ml. chloroform was treated dropwise, while stirring, with a solution of 2 g. bromine in 20 ml. chloroform at 20°C. over the course of an hour. The reaction mixture was subsequently stirred for 4 hours, then washed with water and with an aqueous solution of sodium bisulphite, dried over anhydrous sodium sulphate and then evaporated to dryness. The residue was taken up in 10 ml. benzene and filtered through a thick pad of alumina (20 g.) which was further eluted with 50 ml. benzene. The solvent was removed from the eluant and the residue (1.3 g.) was crystallised from ether-petroleum ether (1:2) at −10°C. to give erythro-3,3′-dibromo-4,4′-dihydroxy-α-methyl-α′-trifluoroethyl-bibenzyl, which had a melting point of 40° – 42°C.

b. A solution of 50 mg. of this dichloro compound in 5 ml. ether was treated with excess diazomethane at 20°C. for 4 hours, whereafter unreacted diazomethane was decomposed with acetic acid. The ether was evaporated off and the residue (50 mg.) was crystallised from etherpetroleum ether (1:1) to give erythro-3,3′-dibromo-4,4′-dimethoxy-α-methyl-α′-trifluoroethyl-bibenzyl, which had a melting point of 139° – 141°C.

Example 6.

To a solution of 2 g. erythro-4,4′-dihydroxy-α-methyl-α′-trifluoroethyl-bibenzyl (see Example 1) in 30 ml. ether was added dropwise, while stirring, 2 g. sulphuryl chloride in 20 ml. ether. The reaction mixture was stirred at 20°C. until thin layer chromatography showed that the reaction was complete. The reaction mixture was then washed with water and with an aqueous solution of sodium bisulphite. The ethereal solution was then dried and the ether removed to give erythro-3,3′-dichloro-4,4′-dihydroxy-αmethyl-α′-trifluoroethyl-bibenzyl in the form of an oil which was purified by filtering a benzene solution thereof through a thick pad of alumina (20 g.). The benzene was distilled off from the eluate to give 1.4 g. of oil which was mixed with 10 ml. pyridine and 10 ml. acetic anhydride and left to react at ambient temperature for 20 hours, whereafter the reaction mixture was poured into ice-dilute hydrochloric acid. The product was isolated by extraction with ether. Removal of the ether from the extract and crystallisation of the residue from ethanol gave erythro-3,3′-dichloro-4,4′-diacetoxy-α-methyl-α′-trifluoroethyl-bibenzyl, which had a melting point of 95° – 96.5°C.

EXAMPLE 7.

A solution of 100 mg. erythro-3,3′-dichloro-4,4′-dihydroxy-α-methyl-α′-trifluoroethyl-bibenzyl (see Example 6) in 5 ml. ether was treated with excess diazomethane at ambient temperature for 4 hours. Excess diazomethane was then destroyed with acetic acid and the solvent was removed. Crystallisation of the residue from ether-petroleum ether (1:1) gave erythro-3,3′-dichloro-4,4′-dimethoxy-α-methyl-α′-trifluoroethyl-bibenzyl, which had a melting point of 129° – 131°C.

The present invention also includes within its scope pharmaceutical compositions containing one or more of the new compounds. These pharmaceutical compositions can be administered orally or parenterally in admixture with a solid or liquid pharmaceutical carrier.

Solid compositions for oral administration include compressed tablets, pills, dispersible powders and granules. In such solid compositions, at least one active compound according to the present invention is admixed with at least one inert diluent, such as tribasic calcium phosphate (Ca$_3$(PO$_4$)$_2$), starch, lactose, gelatine, acacia, sucrose, stearic acid, talc, algenic acid or sodium alginate. The compositions may also comprise, as is normal practice, additional substances other than inert diluents, for example, lubricating agents, such as magnesium stearate, as well as sweetening or flavouring agents.

The percentage of active ingredient in the compositions of the present invention may be varied, it being necessary that it should constitute a proportion such that a suitable dosage for the desired therapeutic effect shall be obtained. In general, the preparations of the present invention should be administered in an effective dose from about 0.00001 mg. to 1 mg. of active substance per kg. of body weight per day.

The following Example illustrates a pharmaceutical composition according to the present invention:-

EXAMPLE 8.

Ingredients for the preparation of 100,000 tablets, each containing 20 g. of active material:

| | |
|---|---|
| erythro-4,4'-difluoro-α-methyl-α'-trifluoroethyl-bibenzyl | 2.00 g. |
| lactose | 3900.00 g. |
| starch | 998.00 g. |
| magnesium stearate | 100.00 g. |

The lactose was first milled to a fine powder and sieved into the bowl of a planetary or trough mixer. The bibenzyl derivative was dissolved in 100 ml. ethanol and mixed with the lactose, mixing being continued for 30 minutes. The starch was sieved and sufficient pure water added thereto to give a 10% by weight starch paste. After subtracting the amount needed for granulation, the remainder of the starch paste was introduced into the mixing vessel and mixing continued for 15 minutes. Granulation was then carried out with the calculated quantity of starch paste at ambient temperature and mixing continued for a further 15 minutes.

The granulate obtained was sieved through a 16 mesh screen, laid out in a thin layer and dried for 12 hours with forced ventilation at a temperature of 35° — 40°C. The dried granulate was then sieved through a 20 mesh screen and returned to the planetary or trough mixer. The magnesium stearate was then sieved through a 60 mesh screen, added to the granulate and mixing continued for 30 minutes. The granulate was then compressed into 50 mg. tablets, each of which contained 20 μg. of the bibenzyl derivative.

When the above tablets are administered to human females after coitus, they prevent the onset of pregnancy.

I claim:

1. A compound of the formula:

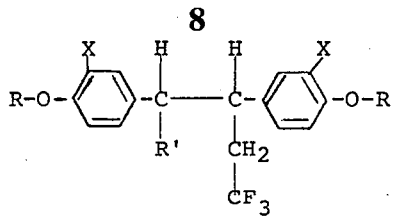

wherein R is a hydrogen or alkyl of up to 3 carbon atoms or alkanoyl of up to 3 carbon atoms, X is hydrogen, fluorine, chlorine or bromine and R' is alkyl of up to 3 carbon atoms.

2. A compound according to claim 1, which is erythro-4,4'-dimethoxy-α-methyl-α'-trifluoroethyl-bibenzyl.

3. A compound according to claim 1, which is erythro-4,4'-dihydroxy-α-methyl-α'-trifluoroethyl-bibenzyl.

4. A compound according to claim 1, which is erythro-3,3'-difluoro-4,4'-dimethoxy-α-methyl-α'-trifluoroethyl-bibenzyl.

5. A compound according to claim 1, which is erythro-3,3'-difluoro-4,4'-dihydroxy-α-methyl-α'-trifluoroethyl-bibenzyl.

6. A compound according to claim 1, which is erythro-3,3'-difluoro-4,4'-dimethoxy-α-(n-propyl)-α'-trifluoroethyl-bibenzyl.

7. A compound according to claim 1, which is threo-3,3'-difluoro-4,4'-dimethoxy-α-(n-propyl)-α'-trifluoroethyl-bibenzyl.

8. A compound according to claim 1, which is erythro-3,3'-difluoro-4,4'-dihydroxy-α-(n-propyl)-α'-trifluoroethyl-bibenzyl.

9. A compound according to claim 1, which is erythro-4,4'-dimethoxy-α-(n-propyl)-α'-trifluoroethyl-bibenzyl.

10. A compound according to claim 1, which is threo-4,4'-dimethoxy-α-(n-propyl)-α'-trifluoroethyl-bibenzyl.

11. A compound according to claim 1, which is erythro-4,4'-dihydroxy-α-(n-propyl)-α'-trifluoroethyl-bibenzyl.

12. A compound according to claim 1, which is erythro-3,3'-dibromo-4,4'-dihydroxy-α-methyl-α'-trifluoroethyl-bibenzyl.

13. A compound according to claim 1, which is erythro-3,3'-dibromo-4,4'-dimethoxy-α-methyl-α'-trifluoroethyl-bibenzyl.

14. A compound according to claim 1, which is erythro-3,3'-dichloro-4,4'-dihydroxy-α-methyl-α'-trifluoroethyl-bibenzyl.

15. A compound according to claim 1, which is erythro-3,3'-dichloro-4,4'-diacetoxy-α-methyl-α'-trifluoroethyl-bibenzyl.

16. A compound according to claim 1, which is erythro-12 b 3,3'-dichloro-4,4'-dimethoxy-α-methyl-α'-trifluoroethyl-bibenzyl.

* * * * *